(12) United States Patent
Rohani et al.

(10) Patent No.: US 7,567,129 B2
(45) Date of Patent: Jul. 28, 2009

(54) MONOLITHIC FLEXIBLE POWER AMPLIFIER USING INTEGRATED TUNABLE MATCHING NETWORKS

(75) Inventors: Nader Rohani, Scottsdale, AZ (US); Hongtao Xu, Hillsboro, OR (US); Yulin Tan, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 62 days.

(21) Appl. No.: 11/823,937

(22) Filed: Jun. 29, 2007

(65) Prior Publication Data
US 2009/0002077 A1  Jan. 1, 2009

(51) Int. Cl.
*H03F 3/191* (2006.01)
(52) U.S. Cl. .................... 330/305; 455/127.1
(58) Field of Classification Search ............ 330/302, 330/310, 295; 375/297; 455/107, 91
See application file for complete search history.

(56) References Cited

U.S. PATENT DOCUMENTS

| 7,092,691 | B2 | 8/2006 | Bohn et al. |
| 7,154,331 | B2 * | 12/2006 | Zaguri ..................... 330/254 |
| 7,157,966 | B2 | 1/2007 | Baree et al. |
| 2004/0224649 | A1 * | 11/2004 | Shamsaifar .............. 455/107 |
| 2008/0180178 | A1 * | 7/2008 | Gao et al. ................. 330/302 |
| 2008/0205548 | A1 * | 8/2008 | Rofougaran ............. 375/297 |
| 2008/0290947 | A1 * | 11/2008 | Dawe ...................... 330/282 |

* cited by examiner

*Primary Examiner*—Robert Pascal
*Assistant Examiner*—Hieu P Nguyen
(74) *Attorney, Agent, or Firm*—The Law Offices of John C. Scott, LLC; John C. Scott

(57) ABSTRACT

A flexible power amplifier can be adapted during operation for use in connection with two or more different wireless standards. In at least one embodiment, adaptations to power transistor size, RF bias current, and matching are made when a corresponding multi-standard wireless device changes the wireless standard under which it is currently operating.

20 Claims, 5 Drawing Sheets

MONOLITHIC FLEXIBLE POWER AMPLIFIER USING INTEGRATED TUNABLE MATCHING NETWORKS

TECHNICAL FIELD

The invention relates generally to power amplifiers and, more particularly, to power amplifiers that can be controllably tuned for operation with different wireless standards.

BACKGROUND OF THE INVENTION

Many modern communication and/or computing devices support wireless communication for multiple different wireless standards. For example, a laptop computer may support wireless networking in accordance with both the IEEE 802.11b, g and IEEE 802.16 wireless networking standards. Often, the various supported standards will involve different operational frequency bands and transmit power levels. Typically, separate circuitry is provided within a device for each of the supported standards. It would be beneficial if one or more circuit components could be shared by multiple different wireless standards to, for example, reduce circuit size and cost.

DETAILED DESCRIPTION

Figure 1:
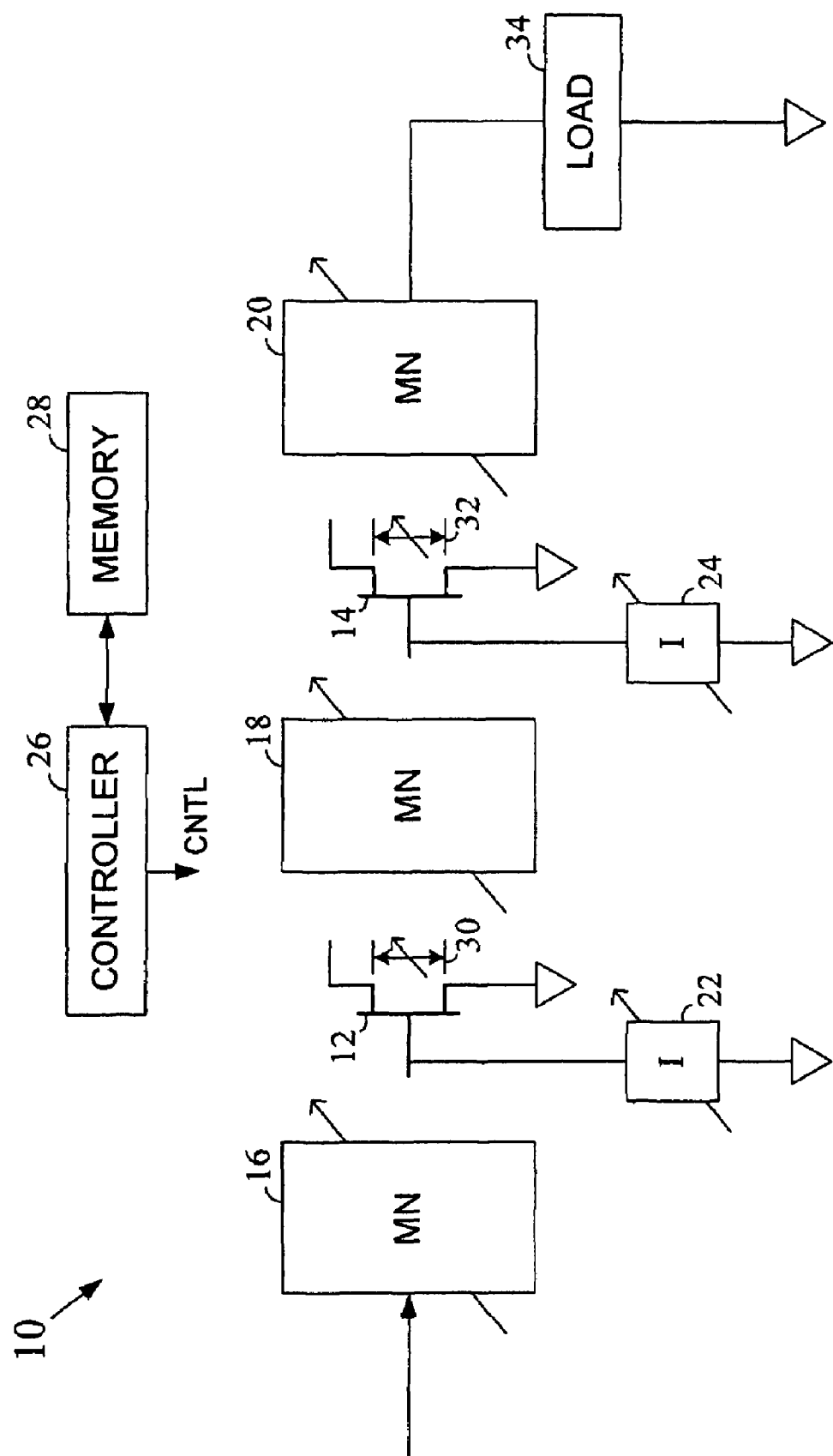
FIG. 1 is a block diagram illustrating an example flexible power amplifier in accordance with an embodiment of the present invention.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein in connection with one embodiment may be implemented within other embodiments without departing from the spirit and scope of the invention. In addition, it is to be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

FIG. 1 is a block diagram illustrating an example flexible power amplifier 10 in accordance with an embodiment of the present invention. In at least one application, the power amplifier 10 is used within a wireless transmitter to generate an amplified signal for transmission into a wireless channel. As will be described in greater detail, the power amplifier 10 can be controllably tuned during operation to work with multiple different wireless standards. When operation within a particular wireless standard is desired, control signals may be delivered to the power amplifier 10 to configure various tunable elements within the amplifier for operation in accordance with the desired standard. The control signals may modify both the operational frequency band of the power amplifier 10 and also the output power level of the power amplifier 10, based on the requirements of the corresponding standard.

As shown in FIG. 1, the power amplifier 10 may include: first and second power transistors 12, 14, a tunable input matching network 16, a tunable inter-stage matching network 18, a tunable output matching network 20, a first bias current control device 22, a second bias current control device 24, a controller 26, and a memory 28. Although a two stage amplifier is shown in the illustrated example, it should be appreciated that other embodiments may include three or more amplification stages. In the illustrated embodiment, the first and second power transistors 12, 14 each have a transistor size 30, 32 that is adjustable. That is, the effective size of the transistors 12, 14 may be modified as needed during amplifier operation by delivering an appropriate control signal or signals thereto (from, e.g., the controller 26). This ability to control the effective size of an active power transistor can be used to vary the current carrying capabilities of the power amplifier 10 as well as to enhance the efficiency of operation of the amplifier under varying application requirements. In some embodiments, only one stage of a power amplifier will include an adjustable power transistor size. In other embodiments, more than one of the amplification stages will include an adjustable transistor size.

The input matching network 16 and the inter-stage matching network 18 include circuitry to provide an input impedance match into the first amplifier stage and an impedance match between the first and second amplifier stages, respectively. In at least one embodiment, each of these matching networks 16, 18 are also tunable for use with multiple operational frequency bands (i.e., bands associated with multiple wireless standards, etc). For example, when the power amplifier 10 is being used to support a first wireless standard, first control signals may be delivered to the input and inter-stage matching networks 16, 18 to provide a match within an operational frequency band associated with the first wireless standard. Likewise, when the power amplifier 10 is being used to support a second wireless standard, second control signals may be delivered to the input and inter-stage matching networks 16, 18 to provide a match within an operational frequency band associated with the second wireless standard, and so on. In other embodiments, one or both of the input and inter-stage matching networks 16, 18 may be non-tunable broadband circuits that work well across the operational frequency ranges of all supported wireless standards. In some embodiments, there may be multiple tunable inter-stage matching networks 18 (e.g., when three or more stages are present).

In at least one embodiment, the tunable output matching network 20 is designed to provide a large signal conjugate power match for each of the supported wireless standards. As above, control signals may be delivered to the matching network 20 to tune it based on a wireless standard currently being implemented. The output of the output matching network 20 will typically be coupled to some form of load 34 (e.g., an antenna, etc.).

As will be described in greater detail, in one approach, controllable switches are used to modify the tunable matching networks for use with the supported wireless standards. In at least one implementation, the same transistor technology (e.g., CMOS, FET, pHEMT, etc.) is used for the controllable switches in the tunable matching networks that is used for the power transistors in the power amplifier to facilitate the implementation of a single chip, monolithic, integrated amplification subsystem. However, in some embodiments, different transistor technologies may be implemented on a common chip (e.g., HBTs as power devices and pHEMTs as tuning elements, etc.). In at least one embodiment of the invention, no varactor or PIN diodes are used as switching or tuning elements to reduce non-linearities and power dissipation, respectively.

The first and second bias current control devices 22, 24 permit the RF bias current of the power devices 12, 14 to be modified in a controllable manner based on a wireless standard currently being implemented. The first and second bias current control devices 22, 24 may each include, for example, one or more transistors, a variable resistor, and/or any other circuit element(s) or structure that allows the amount of bias current flowing through the power transistors 12, 14 to be controlled. As described previously, these elements may be controlled by delivering appropriate control signals to the circuitry therein. Higher bias current may be used when, for example, larger power devices are being used, to generate a high amount of output power. Lower bias current may be used when lower output power is required (e.g., to increase efficiency). In some embodiments, a bias current control device is only used within a single stage of a power amplifier (e.g., the final stage). In other embodiments, all or less than all but more than one power amplifier stage may use a bias current control device.

In at least one embodiment of the present invention, the controller 26 is operative for retrieving configuration information for the various tunable elements within the tunable power amplifier 10 from the memory 28 and for delivering corresponding control signals to the tunable elements (e.g., the matching networks 16, 18, 20, the adjustable size power transistors 12, 14, and the bias current control devices 22, 24 in FIG. 1, etc.). Any type of digital data storage or semiconductor memory may be used as the memory 28, preferably a non-volatile form of storage. When the controller 26 determines that a particular wireless standard is to be used, it may retrieve the corresponding configuration data from the memory 28 and deliver control signals to the tunable elements of the power amplifier 10 based thereon. After the tunable elements have been configured, the power amplifier 10 may begin to process signals in accordance with the particular wireless standard.

In at least one embodiment of the invention, the controller 26 is implemented using a digital processing device such as, for example: a general purpose microprocessor, a digital signal processor (DSP), a field programmable gate array (FPGA), an application specific integrated circuit (ASIC), a microcontroller, a reduced instruction set computer (RISC), a complex instruction set computer (CISC), and/or others. The controller 26 may be part of the power amplifier chip or separate from the chip. In at least one embodiment, the controller 26 is coupled to control inputs of the matching networks 16, 18, 20; the adjustable size power transistors 12, 14; and the bias current control devices 22, 24.

Figure 2:
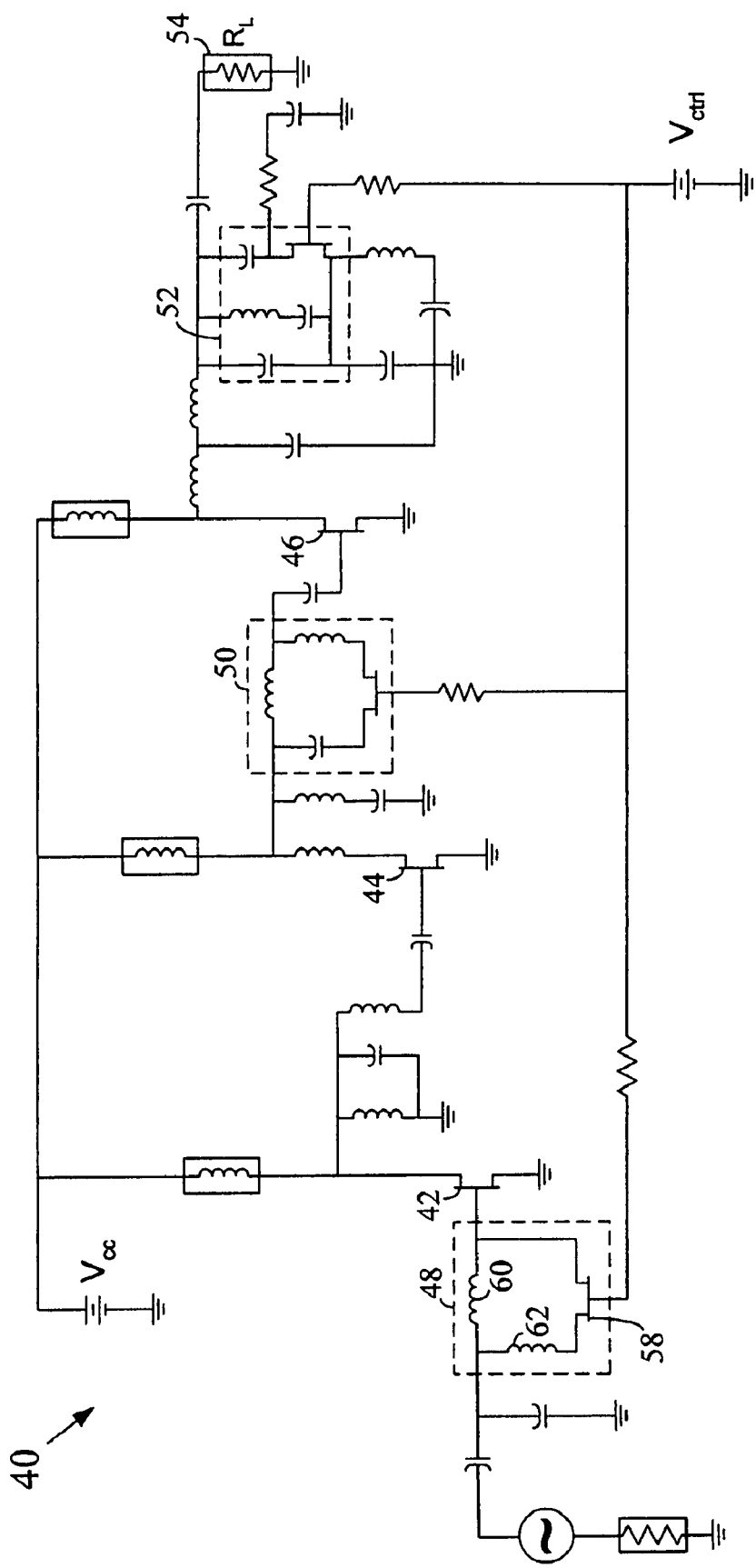
FIG. 2 is an electrical schematic illustrating an example flexible power amplifier in accordance with an embodiment of the present invention.

FIG. 2 is a schematic diagram illustrating an example flexible power amplifier 40 in accordance with an embodiment of the present invention. As shown, the power amplifier 40 includes first, second, and third power transistors 42, 44, 46; a tunable input matching network 48; a tunable inter-stage matching network 50; a tunable output matching network 52, as well as other matching elements. The power amplifier 40 feeds a load resistance ($R_L$) 54. In at least one embodiment, the load resistance 54 is an antenna, although other load types also exist. The power amplifier 40 is a three stage amplifier having an input stage (with power transistor 42), an intermediate stage (with power transistor 44), and an output stage (with power transistor 46). In the illustrated embodiment, the inter-stage matching between the input and intermediate stages of the power amplifier 40 is non-tunable, although in other embodiments tuning devices may be provided in this network as well.

The power amplifier 40 is designed to provide transmit power amplification for two different wireless standards (e.g., IEEE 802.11 a and IEEE 802.11b,g, etc.). Switching elements within the tunable matching networks 48, 50, and 52 may be used to modify the circuit configuration of the matching networks for operation within the supported standards. For example, a transistor switch 58 within input matching network 48 may be turned "on" for operation within a first wireless standard and "off" for operation within a second wireless standard. When the transistor switch 58 is "on," the parallel combination of inductor 60 and inductor 62 may provide a good input match into power transistor 42 within the operational frequency band of the first wireless standard. Similarly, when the transistor switch 58 is "off," inductor 60 alone may provide a good input match into power transistor 42 for the operational frequency band of the second wireless networking standard. The tunable inter-stage matching network 50 may operate in a similar manner. The tunable output matching network 52 is designed to provide, in addition to a good frequency response, a conjugate power match at the output of the power amplifier 40 for each supported wireless standard, to enhance the transfer of power to the load 54. In one implementation, the same transistor technology is used for both the switching elements within the tunable matching networks 48, 50, and 52 and the first, second, and third power transistors 42, 44, 46.

In at least one embodiment of the invention, one or more of the first, second, and third power transistors 42, 44, 46 have a tunable transistor size. This tunable transistor size may be taken advantage of to, for example, handle differences in output power requirements between the supported standards in an efficient manner. For example, for a wireless standard that requires a relatively high transmit power level, a larger final power transistor 46 may be used. For another wireless standard that requires less transmit power, a smaller final power transistor 46 may be used to increase efficiency. In at least one embodiment of the invention, changes in transistor size are implemented by providing multiple power transistors in a parallel arrangement for a particular amplifier stage. The transistors may then be switched into and out of the parallel connection using switching devices to vary the effective size of the overall device. In at least one embodiment of the invention, one or more of the first, second, and third power transistors 42, 44, 46 also have a tunable RF bias current. This tunable RF bias current may also be used to vary transistor power handling capability in an efficient manner.

Figure 3:
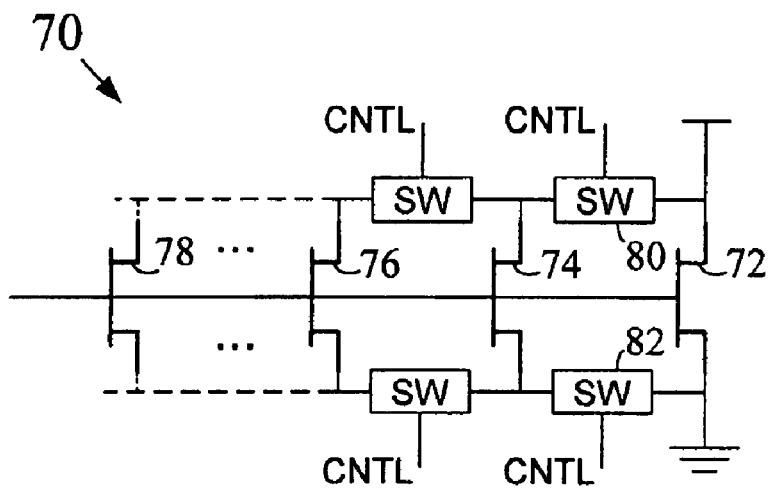
FIG. 3 is a block diagram illustrating an example circuit arrangement for use in providing a tunable transistor size in accordance with an embodiment of the present invention.

FIG. 3 is a block diagram illustrating an example circuit arrangement 70 for use in providing a tunable RF power transistor size in accordance with an embodiment of the present invention. The circuit arrangement 70 may, for example, be used for one or more of the first, second, and third power transistors 42, 44, 46 of FIG. 2. As shown in FIG. 3, a number of power transistors 72, 74, 76, 78 are connected in a parallel configuration with the gate terminals of the transistors 72, 74, 76, 78 coupled together. A first transistor 72 is always active for performing power amplification within the corresponding power amplifier stage. The other transistors 74, 76, 78 may be controllably switched into and out of the power amplifier stage based on a wireless standard currently being implemented. A first switching element 80 is connected between a drain terminal of the first transistor 72 and a drain terminal of the second transistor 74. Likewise, a second switching element 82 is connected between a source terminal of the first transistor 72 and a source terminal of the second transistor 74. Each switching element 80, 82 may include a control terminal to receive a control signal from a corresponding control signal source (e.g., controller 26 in FIG. 1).

When it is desired to increase the transistor size of a corresponding power amplifier stage, the first and second switching elements 80, 82 may be closed (e.g., a transistor switch may be turned "on") to couple the drain and source terminals of the second transistor 74 to those of the first transistor 72. This effectively doubles the size of the power transistor within the power amplifier. Additional switching elements are provided for each additional power transistor 76, 78 within the parallel arrangement. Any number of power transistors (i.e., two or more) may be interconnected in this manner. In at least one embodiment, the switching elements 80, 82 are transistors that use the same transistor technology as the power transistors 72, 74, 76, 78 to simplify integration. However, embodiments using different technologies for the switching elements and the power transistors also exist. In at least one embodiment, the individual power transistors 72, 74, 76, 78 within the circuit arrangement 70 are all the same size. In other embodiments, different size devices are used. Other circuit arrangements for providing a tunable power transistor size may alternatively be used.

Figure 4:
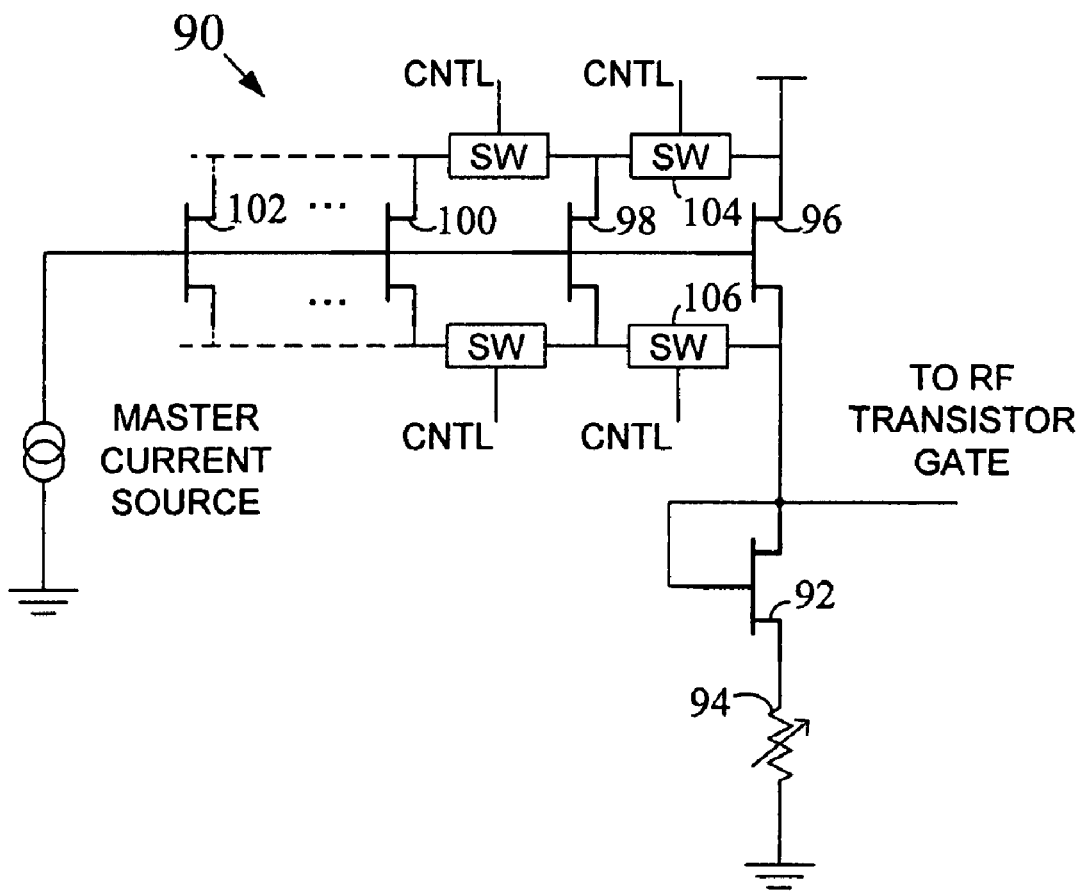
FIG. 4 is a block diagram illustrating an example circuit arrangement for use in providing a tunable RF bias current in accordance with an embodiment of the present invention.

FIG. 4 is a block diagram illustrating an example circuit arrangement 90 for use in providing a tunable RF bias current in accordance with an embodiment of the present invention. The circuit arrangement 90 may be used, for example, for one or more of the first and second bias current control devices 22, 24 of FIG. 1. As in FIG. 3, the circuit arrangement 90 includes a number of transistors 96, 98, 100, 102 connected in a parallel configuration with switching elements 104, 106 connected between adjacent transistor pairs. Operation of this parallel configuration of devices is similar to that described above for the arrangement 70 of FIG. 3. In addition, a transistor 92 may be connected between the source terminal of the first power transistor 96 and ground. A gate terminal of the transistor 92 may be connected to a drain terminal thereof. A variable resistor 94 may also be provided between the source terminal of the first power transistor 96 and ground. In at least one embodiment, the value of the variable resistor 94 is controlled by the controller 26. In other embodiments, a fixed resistor 94 (or no resistor) may be used. The drain terminal of the transistor 92 may be coupled to the gate of the corresponding RF power transistor to provide an RF bias current.

Figure 5:
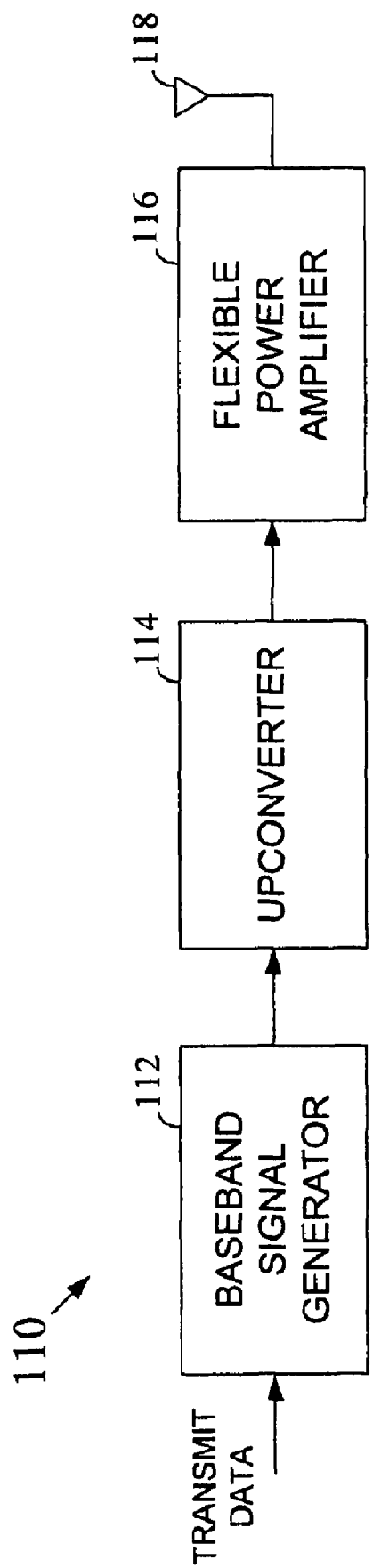
FIG. 5 is a block diagram illustrating the use of a flexible power amplifier within a wireless communication device in accordance with an embodiment of the present invention.

FIG. 5 is a block diagram illustrating the use of a flexible power amplifier within an example wireless communication device 110 in accordance with an embodiment of the present invention. As shown, the wireless communication device 110 includes: a baseband signal generator 112, an upconverter 114, and a flexible power amplifier 116. The output of the flexible power amplifier 116 may be coupled to a transmit antenna 118 to transmit a signal to a remote wireless entity through a corresponding wireless channel. Any type of antenna may be used including, for example, a dipole, a patch, a helical antenna, an antenna array, and/or others. The flexible power amplifier 116 may be an amplifier such as those described previously. The baseband signal generator 112 receives raw transmit data at an input thereof and converts the data to a baseband signal in an appropriate format for transmission. The upconverter 114 then upconverts the baseband signal to an appropriate frequency range for transmission. The flexible power amplifier 116 then amplifies the upconverted signal by a desired amount. The data format output by the baseband signal generator 112 will typically depend upon the wireless standard currently being used. This wireless standard may change during device operation. The operational frequency range that the upconverter 114 converts to may also depend upon the wireless standard currently being implemented. As described previously, the flexible power amplifier 116 may be re-configured during operation to reflect changes in the wireless standard currently being implemented.

Figure 6:
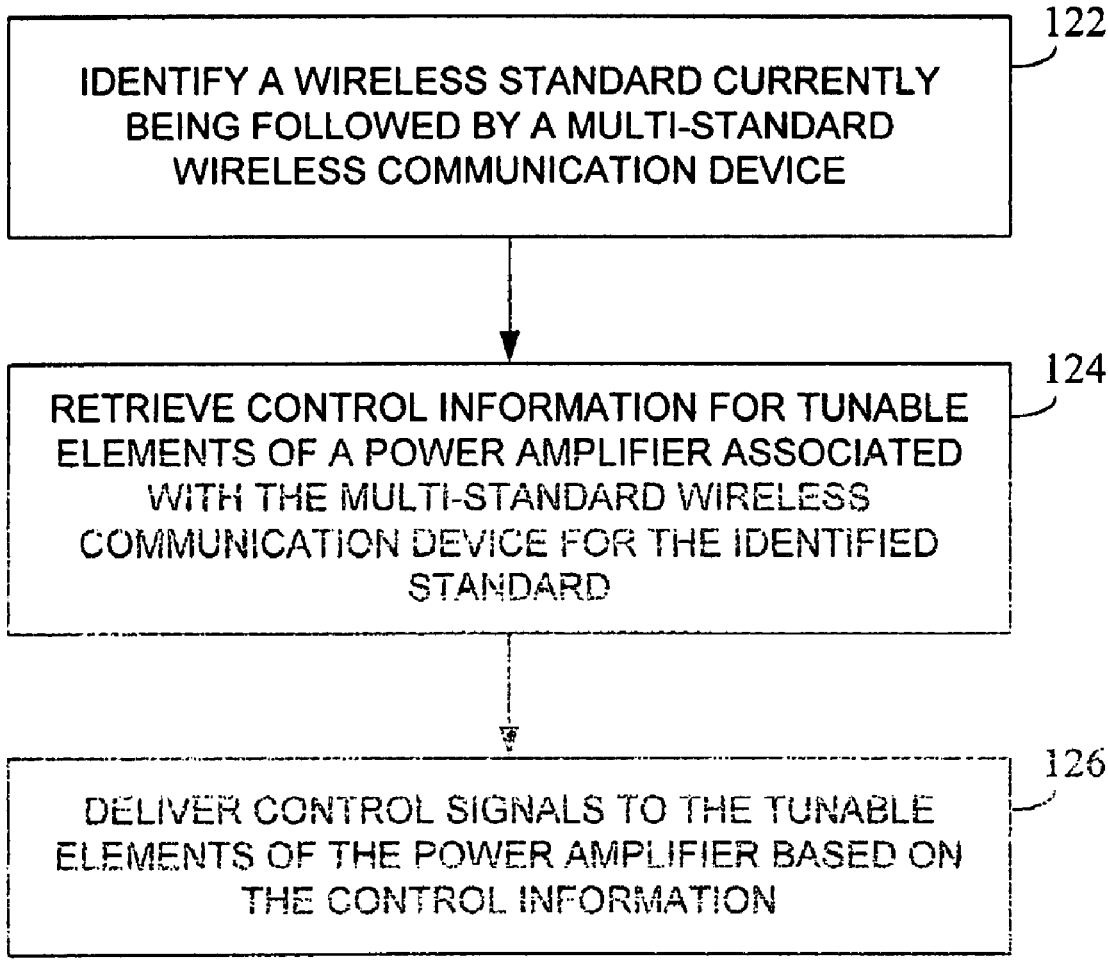
FIG. 6 is a flowchart illustrating an example method for operating a multi-standard wireless communication device in accordance with an embodiment of the present invention.

FIG. 6 is a flowchart illustrating an example method 120 for operating a multi-standard wireless communication device in accordance with an embodiment of the present invention. The multi-standard wireless communication device includes a flexible power amplifier, such as those described previously, within a radio frequency (RF) transmitter thereof. First, a wireless standard that is currently being used by the multi-standard wireless communication device is identified (block 122). For example, if the multi-standard wireless communication device is designed to support both the IEEE 802.11a and the IEEE 802.11b,g wireless networking standards, the standard (e.g., IEEE 802.11a) that the device is presently being configured to support will be identified. After the standard has been identified, control information may be retrieved for tunable elements within the flexible power amplifier for the identified standard (block 124). The information may be retrieved from, for example, a memory within the multi-standard wireless communication device. The tunable elements within the power amplifier for which control information is retrieved may include, for example: (a) a power transistor arrangement having a tunable transistor size within an output stage of the power amplifier (e.g., transistor 14 in FIG. 1); (b) a tunable RF bias current control device to control an RF bias current flowing through the power transistor arrangement (e.g., bias current control device 24 in FIG. 1); and (c) a tunable output matching network to provide a large signal conjugate output power match for the power transistor arrangement (e.g., tunable matching network 20 in FIG. 1). In other embodiments, the tunable elements may also (or alternatively) include similar elements within an input stage of the power amplifier and/or within an intermediate stage of the power amplifier, if any (see, e.g., FIG. 2-4).

After the control information has been retrieved, control signals may be delivered to the tunable elements of the flexible power amplifier (block 126); The control signals will be based upon the retrieved control information. For example, in one possible embodiment, a control bit of logic one may be retrieved for a switching device within a tunable output matching network of a power amplifier for a first wireless standard. This control bit may signify that the switching device is to be in an "on" state. A control signal may then be delivered to the switching device that turns the device on. Similar control signals may be delivered to the other tunable elements within the flexible power amplifier.

The techniques and structures of the present invention may be implemented in any of a variety of different forms. For example, features of the invention may be embodied within laptop, palmtop, desktop, and tablet computers having wireless capability; personal digital assistants (PDAs) having wireless capability; cellular telephones and other handheld wireless communicators; pagers; satellite communicators; cameras having wireless capability; audio/video devices having wireless capability; network interface cards (NICs) and other network interface structures; base stations; wireless access points; power amplifier integrated circuits; as instructions and/or data structures stored on machine readable media; and/or in other formats. Examples of different types of machine readable media that may be used include floppy diskettes, hard disks, optical disks, compact disc read only memories (CD-ROMs), digital video disks (DVDs), Blu-ray disks, magneto-optical disks, read only memories (ROMs), random access memories (RAMs), erasable programmable ROMs (EPROMs), electrically erasable programmable ROMs (EEPROMs), magnetic or optical cards, flash memory, and/or other types of media suitable for storing electronic instructions or data.

In the foregoing detailed description, various features of the invention are grouped together in one or more individual embodiments for the purpose of streamlining the disclosure. This method of disclosure is not to be interpreted as reflecting an intention that the claimed invention requires more features than are expressly recited in each claim. Rather, as the following claims reflect, inventive aspects may lie in less than all features of each disclosed embodiment.

Although the present invention has been described in conjunction with certain embodiments, it is to be understood that modifications and variations may be resorted to without departing from the spirit and scope of the invention as those skilled in the art readily understand. Such modifications and variations are considered to be within the purview and scope of the invention and the appended claims.

What is claimed is:

1. An apparatus comprising:
   a power amplifier having an output power amplification stage including:
   a power transistor arrangement having a tunable transistor size;
   a tunable RF bias current control device to control an RF bias current flowing through said power transistor arrangement; and
   a tunable output matching network to provide a large signal conjugate output power match for said power transistor arrangement; and
   a controller coupled to said power transistor arrangement, said tunable RF bias current control device, and said tunable output matching network to control said transistor size of said power transistor arrangement, said RF bias current of said power transistor arrangement, and said output match of said power transistor arrangement based on a wireless standard currently being followed by a corresponding multi-standard wireless communication device.

2. The apparatus of claim 1, wherein said power transistor arrangement having a tunable transistor size includes:
   at least a first power transistor and a second power transistor;
   a first switching element between a source terminal of said first power transistor and a source terminal of said second power transistor; and
   a second switching element between a drain terminal of said first power transistor and a drain terminal of said second power transistor;
   wherein said first power transistor operates alone when said first and second switching elements are open and said first and second power transistors operate in parallel when said first and second switching elements are closed.

3. The apparatus of claim 1, wherein:
   said tunable RF bias current control device includes a transistor connected between said power transistor arrangement and ground.

4. The apparatus of claim 1, wherein:
   said tunable RF bias current control device includes a variable resistor connected between said power transistor arrangement and ground.

5. The apparatus of claim 1, wherein said power amplifier further includes an input power amplification stage comprising:
   a second power transistor arrangement having a tunable transistor size;
   a second tunable RE bias current control device to control an RF bias current flowing through said second power transistor arrangement; and
   a tunable input matching network to provide an input impedance match for said second power transistor arrangement;
   wherein said controller is coupled to said second power transistor arrangement, said second tunable RF bias current control device, and said tunable input matching network to control said transistor size of said second power transistor arrangement, said RF bias current of said second power transistor arrangement, and said input impedance match of said second power transistor arrangement based on said wireless standard currently being followed by said corresponding multi-standard wireless communication device.

6. The apparatus of claim 5, wherein said power amplifier further includes an intermediate power amplification stage between said input and output power amplification stages, said intermediate power amplification stage comprising:
   a third power transistor arrangement having a tunable transistor size;
   a third tunable RF bias current control device to control an RF bias current flowing through said second power transistor arrangement; and
   a tunable inter-stage matching network to provide a tunable impedance match between said intermediate power amplification stage and said output power amplification stage;
   wherein said controller is coupled to said third power transistor arrangement, said third tunable RF bias current control device, and said tunable inter-stage matching network to control said transistor size of said third power transistor arrangement, said RF bias current of said third power transistor arrangement, and said impedance match between said intermediate power amplification stage and said output power amplification stage based on said wireless standard currently being followed by said corresponding multi-standard wireless communication device.

7. The apparatus of claim 1, wherein:
   said tunable output matching network includes a tuning switch that is turned on and off to tune said output matching network, wherein said tunable output matching network provides a large signal conjugate output power match for an operational frequency band of a first wireless standard when said tuning switch is on and said tunable output matching network provides a large signal conjugate output power match for an operational frequency band of a second wireless standard when said tuning switch is off.

8. A method comprising:
identifying a wireless standard currently being followed by a multi-standard wireless communication device;
retrieving control information for tunable elements of a power amplifier of said multi-standard wireless communication device based on said identified wireless standard, said tunable elements including: a first power transistor arrangement having a tunable transistor size; a tunable RF bias current control device to control an RF bias current flowing through said first power transistor arrangement; and a tunable output matching network to provide a large signal conjugate output power match for said first power transistor arrangement, wherein said first power transistor arrangement, said tunable RF bias current control device, and said tunable output matching network are within an output stage of said power amplifier; and
delivering control signals to said tunable elements of said power amplifier based on said control information.

9. The method of claim 8, wherein said tunable elements further include:
a second power transistor arrangement having a tunable transistor size;
a second tunable RF bias current control device to control an RF bias current flowing through said second power transistor arrangement; and
a tunable input matching network to provide an input match into said second power transistor arrangement;
wherein said second power transistor arrangement, said second tunable RF bias current control device, and said tunable input matching network are within an input stage of said power amplifier.

10. The method of claim 9, wherein said tunable elements further include:
a third power transistor arrangement having a tunable transistor size;
a third tunable RF bias current control device to control an RF bias current flowing through said third power transistor arrangement; and
a tunable inter-stage matching network to provide an impedance match between said third power transistor arrangement and said first power transistor arrangement;
wherein said third power transistor arrangement, said third tunable RF bias current control device, and said tunable inter-stage matching network are within an intermediate stage of said power amplifier between said input stage and said output stage.

11. The method of claim 8, wherein:
said tunable output matching network includes a tuning switch that is turned on and off to tune said output matching network, wherein said tunable output matching network provides a large signal conjugate output power match for an operational frequency band of a first wireless standard when said tuning switch is on and said tunable output matching network provides a large signal conjugate output power match for an operational frequency band of a second wireless standard when said tuning switch is off.

12. The method of claim 8, wherein:
said tunable RF bias current control device includes a transistor connected between said first power transistor arrangement and ground.

13. The method of claim 8, wherein:
said tunable RF bias current control device includes a variable resistor connected between said first power transistor arrangement and ground.

14. A wireless communication device comprising:
a dipole antenna to transmit a signal into a wireless channel;
a power amplifier coupled to deliver an amplified transmit signal to said dipole antenna, said power amplifier having an output power amplification stage including:
a power transistor arrangement having a tunable transistor size;
a tunable RF bias current control device to control an RF bias current flowing through said power transistor arrangement; and
a tunable output matching network to provide a large signal conjugate output power match for said power transistor arrangement; and
a controller coupled to said power transistor arrangement, said tunable RF bias current control device, and said tunable output matching network to control said transistor size of said power transistor arrangement, said RF bias current of said power transistor arrangement, and said output match of said power transistor arrangement based on a wireless standard currently being followed by a corresponding multi-standard wireless communication device.

15. The device of claim 14, wherein said power transistor arrangement having a tunable transistor size includes:
at least a first power transistor and a second power transistor;
a first switching element between a source terminal of said first power transistor and a source terminal of said second power transistor; and
a second switching element between a drain terminal of said first power transistor and a drain terminal of said second power transistor;
wherein said first power transistor operates alone when said first and second switching elements are open and said first and second power transistors operate in parallel when said first and second switching elements are closed.

16. The device of claim 14, wherein:
said tunable RF bias current control device includes a transistor connected between said power transistor arrangement and ground.

17. The device of claim 14, wherein:
said tunable RF bias current control device includes a variable resistor connected between said power transistor arrangement and ground.

18. The device of claim 14, wherein said power amplifier further includes an input power amplification stage comprising:
a second power transistor arrangement having a tunable transistor size;
a second tunable RF bias current control device to control an RF bias current flowing through said second power transistor arrangement; and
a tunable input matching network to provide an input impedance match for said second power transistor arrangement;
wherein said controller is coupled to said second power transistor arrangement, said second tunable RF bias current control device, and said tunable input matching network to control said transistor size of said second power transistor arrangement, said RE bias current of said second power transistor arrangement, and said input impedance match of said second power transistor arrangement based on said wireless standard currently being followed by said corresponding multi-standard wireless communication device.

19. The device of claim 18, wherein said power amplifier further includes an intermediate power amplification stage between said input and output power amplification stages, said intermediate power amplification stage comprising:
- a third power transistor arrangement having a tunable transistor size;
- a third tunable RF bias current control device to control an RF bias current flowing through said second power transistor arrangement; and
- a tunable inter-stage matching network to provide a tunable impedance match between said intermediate power amplification stage and said output power amplification stage;
- wherein said controller is coupled to said third power transistor arrangement, said third tunable RF bias current control device, and said tunable inter-stage matching network to control said transistor size of said third power transistor arrangement, said RF bias current of said third power transistor arrangement, and said impedance match between said intermediate power amplification stage and said output power amplification stage based on said wireless standard currently being followed by said corresponding multi-standard wireless communication device.

20. The device of claim 14, wherein:
said tunable output matching network includes a tuning switch that is turned on and off to tune said output matching network, wherein said tunable output matching network provides a large signal conjugate output power match for an operational frequency band of a first wireless standard when said tuning switch is on and said tunable output matching network provides a large signal conjugate output power match for an operational frequency band of a second wireless standard when said tuning switch is off.

* * * * *